(12) United States Patent
Adams et al.

(10) Patent No.: US 9,922,517 B2
(45) Date of Patent: *Mar. 20, 2018

(54) PRE-SMOKE DETECTOR AND SYSTEM FOR USE IN EARLY DETECTION OF DEVELOPING FIRES

(71) Applicant: Nevada Nanotech Systems Inc., Sparks, NV (US)

(72) Inventors: Jesse D. Adams, Reno, NV (US); Ralph G. Whitten, Reno, NV (US)

(73) Assignee: Nevada Nanotech Systems Inc., Sparks, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/356,282

(22) Filed: Nov. 18, 2016

(65) Prior Publication Data

US 2017/0069187 A1 Mar. 9, 2017

Related U.S. Application Data

(63) Continuation of application No. 13/274,765, filed on Oct. 17, 2011, now Pat. No. 9,547,968.

(Continued)

(51) Int. Cl.
*G08B 17/117* (2006.01)
*G08B 17/10* (2006.01)
(Continued)

(52) U.S. Cl.
CPC ............. *G08B 17/117* (2013.01); *G01N 5/02* (2013.01); *G01N 25/00* (2013.01);
(Continued)

(58) Field of Classification Search
CPC ........ G08B 17/117; G08B 17/10; G01N 5/02; G01N 25/00; G01N 25/4893;
(Continued)

(56) References Cited

U.S. PATENT DOCUMENTS 5,260,687 A 11/1993 Yamauchi et al.
7,105,301 B2 9/2006 Su et al.
(Continued)

OTHER PUBLICATIONS

Ni, M. et al., Orthogonal gas sensor arrays with intelligent algorithms for early warning of electrical fires, Sensors and Actuators B, 2008, pp. 889-899, vol. 130.
(Continued)

*Primary Examiner* — Mohamed Barakat
(74) *Attorney, Agent, or Firm* — TraskBritt

(57) ABSTRACT

A pre-smoke detector and system for use in early detection of developing fires whereby vapors of marker chemicals generated during the melting and/or smoldering of common household materials are detected before detection by conventional smoke detectors. Vapors resulting from heating and resultant vaporization of substances are detected as well as vapors resulting from their breakdown, decomposition, or pyrolysis during the pre-combustion stage. Conventional smoke detectors focus on particle detection and are most effective after a developing fire has produced smoke. To minimize false alarms caused by common household odors, the pre-smoke detectors focus on detecting medium temperature pyrolysis products using sensor coatings that can be consistent with a 10-year operational lifetime and multiple orthogonal detection processes. Since virtually all marker chemicals of interest for pre-smoke detection are heavier than air, a system is described that appropriately integrates with smoke detector alarm systems present in most homes.

22 Claims, 5 Drawing Sheets

Related U.S. Application Data

(60) Provisional application No. 61/455,204, filed on Oct. 15, 2010.

(51) Int. Cl.

| | | |
|---|---|---|
| *G01N 5/02* | (2006.01) | |
| *G01N 25/00* | (2006.01) | |
| *G01N 25/48* | (2006.01) | |
| *G01N 33/00* | (2006.01) | |
| G01N 29/02 | (2006.01) | |
| G01N 1/22 | (2006.01) | |

(52) U.S. Cl.
CPC ..... *G01N 25/4893* (2013.01); *G01N 33/0047* (2013.01); *G08B 17/10* (2013.01); *G01N 1/2214* (2013.01); *G01N 29/022* (2013.01); *G01N 2291/0256* (2013.01)

(58) Field of Classification Search
CPC ............. G01N 33/0047; G01N 1/2214; G01N 29/022; G01N 2291/0256
See application file for complete search history.

(56) References Cited

U.S. PATENT DOCUMENTS

| | | | | |
|---|---|---|---|---|
| 2004/0066278 | A1* | 4/2004 | Hughes ................ | G06F 21/31 340/10.1 |
| 2007/0133485 | A1* | 6/2007 | Tredoux ............... | H04L 67/18 370/338 |
| 2008/0004041 | A1* | 1/2008 | Ahn ..................... | H04W 64/00 455/456.1 |
| 2008/0252473 | A1* | 10/2008 | Fink ..................... | G08B 17/11 340/629 |
| 2009/0082216 | A1 | 3/2009 | Cohn et al. | |
| 2009/0122312 | A1* | 5/2009 | Reddy .................. | G01N 21/77 356/321 |
| 2009/0139340 | A1 | 6/2009 | King et al. | |
| 2010/0000292 | A1* | 1/2010 | Karabacak .......... | G01N 29/022 73/24.01 |
| 2010/0240144 | A1* | 9/2010 | Gilbert ................. | G01N 21/658 436/169 |
| 2012/0092175 | A1 | 4/2012 | Adams et al. | |
| 2012/0133932 | A1* | 5/2012 | Henry ................... | G01J 3/02 356/301 |
| 2012/0198912 | A1* | 8/2012 | Ewing .................. | G01N 1/22 73/23.35 |

OTHER PUBLICATIONS

Ozawa, T. et al., Detection of decomposed compounds from an early stage tire by an adsorption/combustion-type sensor, Sensors and Actuators B, 2005, pp. 473-477, vol. 108.

"Wikipedia:Copyrights", Wikipedia: The Free Encyclopedia, Wikimedia Foundation, Inc., accessed Aug. 1, 2014, <http://en.wikipedia.org/wiki/Wikipedia:Copyrights>, all pages pertinent.

"Differential thermal analysis", Wikipedia: The Free Encyclopedia, Wikimedia Foundation, Inc., last revised: May 28, 2014, accessed Aug. 1, 2014, <http://en.wikipedia.org/wiki/Differential_thermal_analysis>, all pages pertinent—especially the first paragraph.

"Differential thermal analysis: Difference between revisions", Wikipedia: The Free Encyclopedia, Wikimedia Foundation, Inc., last revised: Sep. 30, 2009, accessed Aug. 1, 2014, <http://en.wikipedia.org/w/index.php?title=Differential_thermal_analysis&diff=61 0455806&oldid=317011695>, all pages pertinent—especially the first paragraph.

\* cited by examiner

PRE-SMOKE DETECTOR AND SYSTEM FOR USE IN EARLY DETECTION OF DEVELOPING FIRES

CROSS-REFERENCE TO RELATED APPLICATIONS

This application is a continuation of U.S. patent application Ser. No. 13/274,765, filed Oct. 17, 2011, now U.S. Pat. No. 9,547,968, issued Jan. 17, 2017, and entitled "PRE-SMOKE DETECTOR AND SYSTEM FOR USE IN EARLY DETECTION OF DEVELOPING FIRES," which is a non-provisional application that claims the benefit of U.S. Provisional Application No. 61/455,204, filed Oct. 15, 2010, and entitled "PRE-SMOKE DETECTOR," the disclosure of each of which is hereby incorporated herein in their entirety by reference.

FIELD OF THE INVENTION

This invention relates generally to chemical sensors and, more specifically, to pre-smoke detectors and systems for use in the early detection of fires or potential fires.

BACKGROUND OF THE INVENTION

There are generally two basic types of smoke detectors commonly used today in working and living environments, such as buildings and homes. They are ionization and photoelectric type smoke detectors. The ionization type detector is the most prevalent type of smoke detector and is most responsive to flaming fires. The photoelectric type detector is generally considered more responsive to smoldering fires, which are those that begin with a long period of smoke build-up but no flames. For the best protection, the National Fire Protection Association recommends that both types be installed.

For smoke detection, a combustion aerosol commonly called smoke is composed of particles ranging in size from below those that are visible to those that are readily visible under ordinary light and are what smoke detectors detect. This applies to both the ionization-type smoke detector as well as the photoelectric-type smoke detector. Therefore, both types of smoke detectors can be thought of as particle detectors or, to be more precise, as particle counters.

Depending on the alarm response set point, smoke detectors produce an alarm when a certain number of particles are present within their sensing chambers. This particle-counting ability of the smoke detectors is complicated by the fact that the particle diameter also influences their response. In the case of the photoelectric smoke detectors, the wavelength of light used in the detectors as well as the complex index of refraction of the smoke particles also influences their response.

Statistics published by the U.S. Federal Emergency Management Agency in 2005 show that fires caused by smoking and electrical malfunction account for 29.5% of all deaths, despite only accounting for 10.3% of all fires. Cooking on the other hand, accounts for 39.9% of all fires, but only 5.1% of deaths. Apparently, it is fires that occur when no one is watching or nearby that are the most dangerous. The most prevalent flammable fibers in a home or building are cotton, rayon, nylon, acrylic, polyester, polylactide (PLA), olefin, and polyurethane, while the most prevalent wiring insulation materials are polyvinyl chloride (PVC), polyethylene, rubber, polychloroprene, and TEFLON®. As these materials are heated, melting and/or smoldering thereof eventually creates smoke particles that conventional smoke detectors can detect. However, long before a situation reaches that stage, materials are being heated and evaporated. As the temperature increases, the heated substances begin to vaporize and also decompose, giving off vapors that spread throughout a room or building. If these vapors could be reliably detected before smoke particles are generated, an early warning could undoubtedly save many lives. Indeed, it would be extremely useful to sense or detect and warn of smoldering fabric or electrical insulation before smoke is generated.

With respect to fires or potential fires, materials composed of polymers decompose via a series of chemical reaction mechanisms when heated to a sufficiently high temperature. The main mechanisms that reduce molecular weight of the polymers are random chain scission, chain-end scission (unzipping), and chain stripping (removal of side groups). Two other thermally induced processes, cross-linking and condensation, have the opposite effect of increasing molecular weight. Although decomposition often involves more than one of the scission mechanisms, the dominant reaction in most polymer systems is random chain scission. This commences with the weakest bonds in the chain, which is usually where an irregularity occurs in the molecular structure due, for instance, to the presence of a tertiary carbon atom, as in polypropylene, or other relatively unstable linkages with low dissociation energies. Scission usually proceeds randomly throughout the length of the chain.

With increasing temperature, other chemical bonds with higher dissociation energies rupture, causing the resulting segments to breakdown further into monomers, oligomers (i.e., polymer units with ten or fewer monomer units), and other low molecular weight species. It is noteworthy that while random chain scission can decompose long polymer chains into an extremely large number of fragments, in general, only a few percent of the bonds need to rupture to drastically degrade the mechanical properties. A bond rupture level of about 10% is generally sufficient to generate organic compounds that are volatile in a fire. For fragments to be small enough to diffuse through the polymer char into the fire, fragments molecular weight must be lower than about 400, although with many volatile species the molecular weight (MW) is much less (for example, styrene MW=96). It is these volatiles that decompose at the fire/composite interface that produce heat that sustains the decomposition process.

Chain-end scission (unzipping or depolymerization) is another important decomposition reaction that can compete with random scission in some polymer systems. Here, individual monomer units or volatile chain fragments are successively removed at the chain end until the polymer molecule has completely depolymerized. Chain stripping is a further decomposition reaction that involves the removal of side groups.

Cross-linking results, often temporarily, in an increase in molecular weight, in competition with the processes mentioned above. In most thermosets, for instance, it is well-known that "post-cure" or further cross-linking occurs at elevated temperature (say above 100° C.-150° C.) and precedes the decomposition processes that occur at higher temperatures (typically above 250° C.-400° C.). Likewise, in some thermoplastics (e.g., polyethylene), a degree of cross-linking precedes chain scission.

The thermal decomposition reactions of polymers may proceed by oxidative processes or simply by the action of heat. The decomposition process is often accelerated by oxygen, but in thick composite sections it is generally only the surface region that decomposes in the presence of oxygen. The out-gassing of volatiles from the decomposition zone impedes the ability of oxygen to diffuse much beyond the surface layers of the composite. Therefore, atmospheric oxygen does not have a major influence as the decomposition process moves deep into thick section composites, where decomposition tends to be driven mainly by heat.

Some polymers undergo random chain scission, end-chain scission, and chain stripping reactions, which leads to the loss of hydrogen atoms, pendant groups, and other low molecular weight organic groups from the main chain. These polymers yield a small amount of char (typically 5-20% of the original mass) and they include polyesters, vinyl esters, epoxies and polyvinyl chlorides (PVC).

Yet other polymers are characterized by a high aromatic ring content that decomposes into aromatic fragments that fuse via condensation reactions to produce moderate to high amounts of char. Aromatic rings are the basic building blocks from which char is formed, and, therefore, the higher the aromatic content of the polymer, the higher the char yield. Char yield increases linearly with the concentration of multiple-bonded aromatic ring groups in the polymer system. These aromatic groups are transformed at high temperature into pitch-like entities that eventually combine into char. A well-known polymer from the viewpoint of char formation is phenolic, in which 40-60% of the resin mass is converted to char. Several other polymer systems yield high amounts of char, and these include highly aromatic thermosets (e.g., polyimides, phthalonitriles, epoxy novolacs, and cyanate esters) and certain thermoplastics (e.g., polyphenylene sulfide (PPS), poly(p-phenylene oxide) (PPO), and polyether ether ketone (PEEK)).

Different chemical compounds result from the pyrolysis of household materials depending on the temperature at which they decompose. For instance, high-temperature pyrolysis of neoprene results in a substantial increase in the production of the following hydrocarbons: ethylene, acetylene, ethane, propane, propylene, propyne, n-butane, I-butene, isobutylene, cis-2-butene, trans-2-butene, ethylacetylene, and pentane. The main difference between these high-temperature degradation products and those from medium-temperature pyrolysis is a reduction in the quantity of liquid pyrolyzates, particularly in the lower-molecular-weight compounds. Pyrolysis at medium temperatures for rubber-134 show mainly the production of higher molecular weight aliphatic hydrocarbons, aliphatic alcohols, naphthalene, benzoic, and phthalic acids. Those from rubber-138 are predominantly aromatic.

A device and system that can detect pre-smoke vapors resulting from the vaporization of common household substances or the resultant breakdown, decomposition, or pyrolysis of these substances, could be a vital addition to the normal compliment of smoke detectors that are typically used to warn of fires or potential fires. In the case of fires that result from smoldering while the occupants are asleep, such as fires initiated by electrical malfunction or smoking, a significant decrease in the occurrence rate of both fires and fatalities might be the desirable result.

Accordingly, there is a need for a pre-smoke device or detector that can reliably identify individual analytes that are indicative of a pre-smoke condition, or alternately reliably detect key analytes as a class depending on their characteristics, for use in the early detection and warning of fires or potential fires.

SUMMARY OF THE INVENTION

The present invention is directed to pre-smoke detectors and systems for use in the early detection of fires or potential fires.

The pre-smoke detectors of the present invention detect vapors given off during the early stage of smoldering before smoke particles are given off and a fire begins and can provide an early warning for unsuspecting occupants of a building or home, for example. The pre-smoke detector can reliably detect medium temperature pyrolysis products that occur in the early stages of melting and smoldering as temperatures increase. These chemicals eventually degrade to form high temperature pyrolysis products. However, by that time, smoke particles may be produced. The pre-smoke detector can detect a pre-smoke stage because it is capable of detecting particular sets of chemical types, which includes molecules of materials commonly used in fabrics and wiring insulation, as well as pyrolysis products of those materials resulting from thermal degradation. This contrasts with conventional smoke detectors, which are focused on particle detection.

Also, existing chemical sensing systems tend to focus on a finite number of molecular properties. Some approaches offer individual sensors covering a limited spectrum of analytes with similar properties, while others have a one-to-one correspondence with a specific analyte. The pre-smoke detector approach is quite different. Here, the pre-smoke detector can be constructed so that a wide spectrum of physical and chemical properties of trace vapors and particles are measured via multiple transducers, with multiple transduction methods and transducer parameter modulations. Complex algorithms turn these measured parameters into recognition results. Results can be based on measurement channels having a high degree of orthogonality offering selectivity surpassing other sensing approaches. As a consequence, sensitivity is enhanced and false positives are reduced thereby increasing the reliability of detection. However, it may occur that even a limited number of detection processes and measurement channels provide sufficient detection of marker chemicals indicating a developing fire and, therefore, will be sufficient. Key advantages of the pre-smoke detector are low cost, low power, compact size, very broad spectrum (many analytes detectable), long-term unattended operation, self-cleaning, self-calibrating, minimal consumables, and the ability to detect an analyte after only a brief exposure. The broad spectrum capability of the pre-smoke detector ensures a wide detection range for detecting a variety of chemical substances.

In one embodiment, the pre-smoke detector, which may be referred to herein as a molecular property spectrometer (MPS), can include an array of micro-transducers that are constructed on a single silicon chip, with each transducer having a different chemical sensitive coating and multiple detection methodologies.

In another embodiment, the pre-smoke detector includes a substrate having an array of microcantilevers. Each microcantilever includes a surface coating that adsorbs one or more of types of vaporized pyrolysis products resulting from thermal decomposition of fibers and/or wiring insulation materials. The vaporized pyrolysis products are of a different chemical composition than that of the pre-decomposed fibers and/or wiring insulation materials. An electronic circuit is also provided that includes one or more devices that cooperate with the microcantilevers and are configured to detect and/or analyze the vaporized pyrolysis products. The pre-smoke detector further includes an alarm that is configured to activate if the vaporized pyrolysis products are detected and/or meet or exceed a pre-determined threshold amount. In one example, the pre-smoke detector does not detect smoke particles.

In another embodiment, a system for early detection of a fire or potential fire is provided. The system includes the pre-smoke detector, which does not detect smoke particles, and a smoke detector that detects smoke particles and includes an alarm that is activated if smoke particles are detected and/or meet or exceed a pre-determined threshold amount. The pre-smoke detector and smoke detector are in communication with one another so that when one alarm is signaled the other is signaled.

In yet another embodiment, a method for early detection of a fire or potential fire is provided. The method includes adsorbing one or more of types of vaporized pyrolysis products on a surface coating of one or more microcantilevers. The vaporized pyrolysis products result from thermal decomposition of fibers and/or wiring insulation materials and are of a different chemical composition than that of the pre-decomposed fibers and/or wiring insulation materials. Next, the adsorbed vaporized pyrolysis products are detected and/or analyzed. Then, an alarm is activated if the vaporized pyrolysis products are detected and/or meet or exceed a pre-determined threshold amount.

In still another embodiment, a method for early detection of a fire or potential fire includes using the pre-smoke detector.

BRIEF DESCRIPTION OF THE DRAWINGS

The accompanying drawings, which are incorporated in and constitute a part of this specification, illustrate embodiments of the invention and, together with the general description of the invention given above, and detailed description given below, serve to explain the invention.

DETAILED DESCRIPTION

A pre-smoke detector (PSD) 10 for use in the early detection of fires or potential fires, and a system 12 using the same, is described hereinbelow and shown in FIGS. 1-5B.

Figure 1:
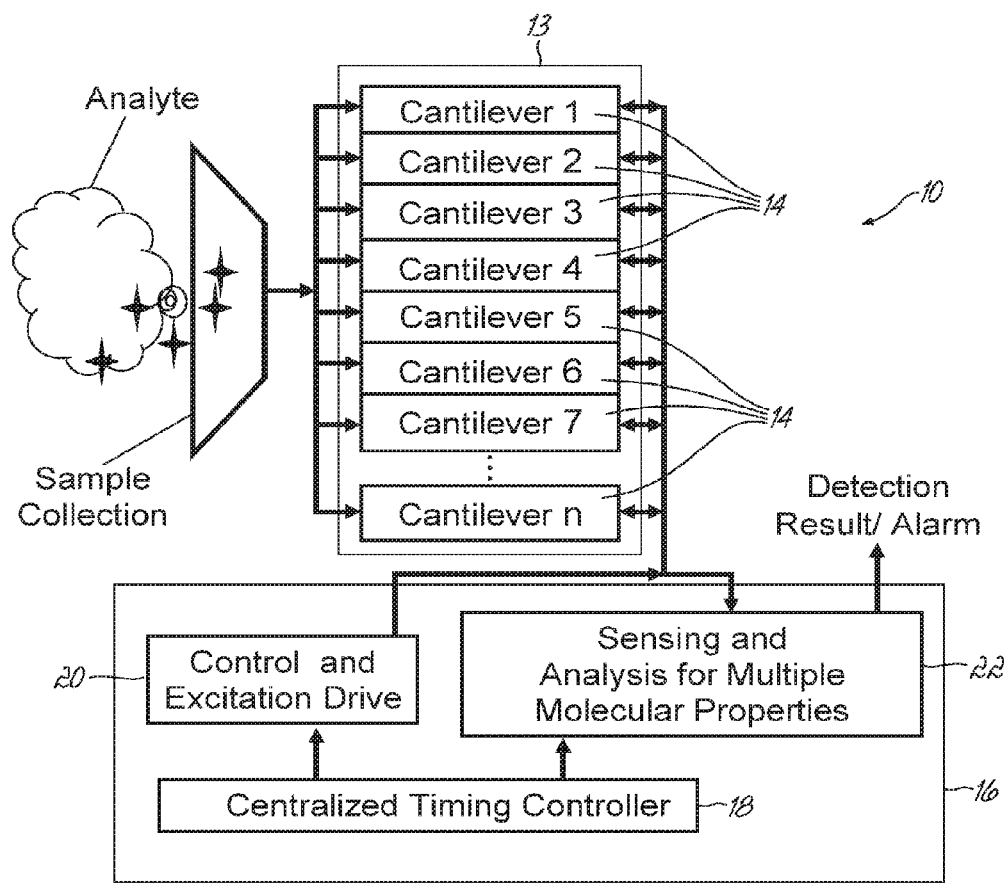
FIG. 1 is a block diagram of a pre-smoke detector in accordance with one embodiment of the present invention.

FIG. 1 shows a block diagram of an embodiment of the pre-smoke detector 10, which may also be referred to herein as a "molecular property spectrometer" (MPS). Here, transducers located on sensor chip 13 of pre-smoke detector 10 define an array of microcantilevers 14. Any desirable number of microcantilevers 14 can be utilized. The array of microcantilevers 14 is coupled to an electronic circuit 16 that includes a centralized timing controller 18, which can include a processor, memory, timing circuits, and suitable hardware and software to run control applications for the microcantilevers 14 and analyze and detect specified analytes for providing early warning of fires or potential fires. As shown, the controller 18 cooperates with drive and sense circuitry 20 and 22 for both excitation and sensing of the array of microcantilevers 14. The drive circuitry 20 can cooperate to drive the microcantilevers 14 into oscillation using any suitable drive element, such as a piezoelectric material 26 (FIG. 2), an electrostatic element, a thermal element, or a magnetic element. Excitation can thus take the form of inducing vibration of the microcantilevers 14, heating of the microcantilevers 14, and otherwise electrically stimulating the microcantilevers 14. The sense circuitry 22 can also cooperate to measure deflection amplitudes of oscillating microcantilevers 14 with any suitable sense element, such as an optical element, and/or the piezoelectric material 26 (FIG. 2), for example, a piezoresistive element, a capacitive element, or a magnetic element. Sensing can take the form of frequency detection, impedance detection, temperature detection, and stress detection, for example.

Figure 2:
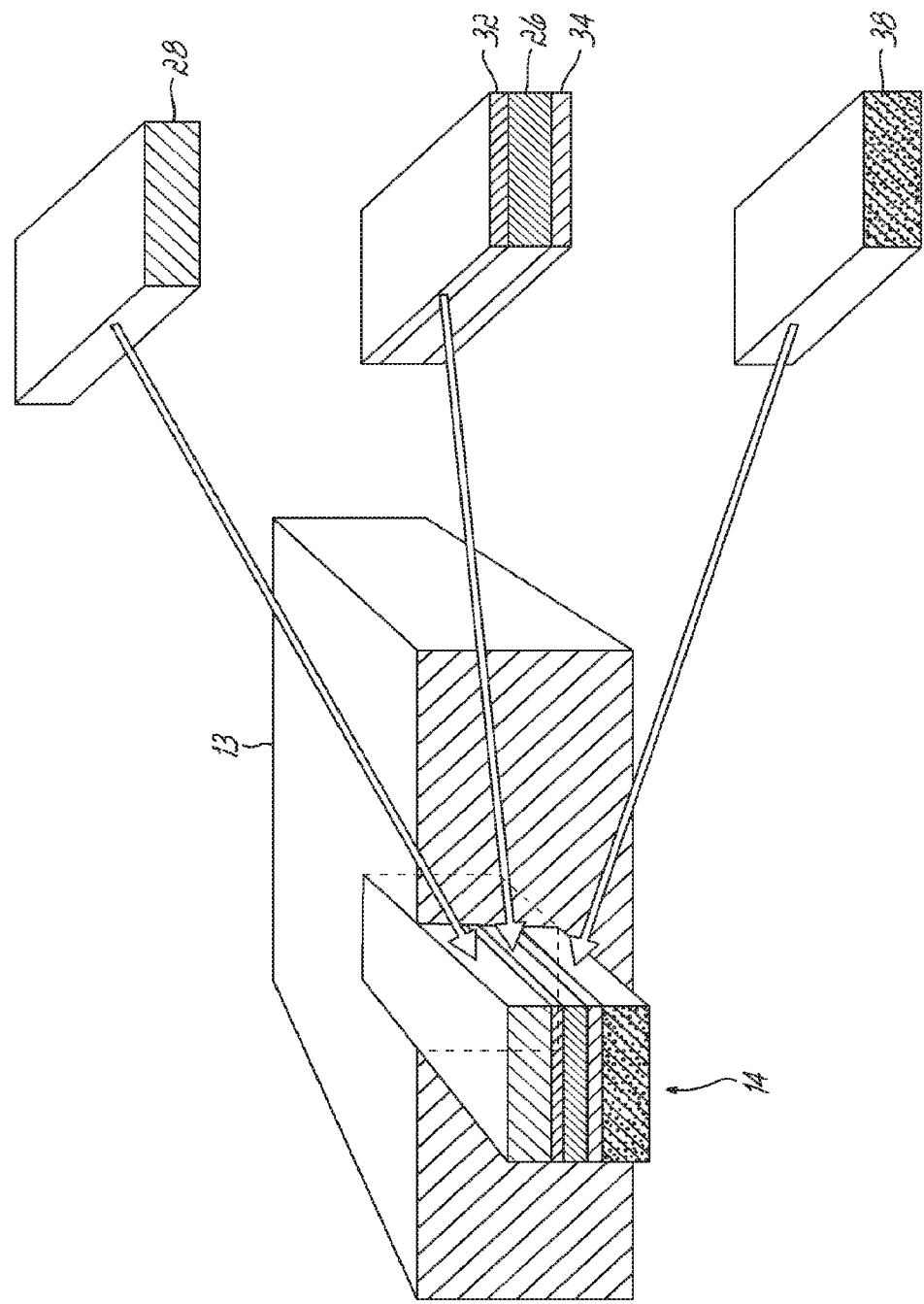
FIG. 2 is a partial cross-section of one embodiment of a microcantilever transducer element for use in the pre-smoke detector of FIG. 2.

With further reference to FIGS. 1 and 2, on the surface of the cantilever 14 is a surface coating or layer 28, which may be an analyte-sensitive polymer, or in a preferred embodiment, a metallic plating or coating such as molybdenum, palladium, gold, platinum, and/or aluminum. Alternately, other materials may be utilized for the surface coating 28 such as silicon, polysilicon, silicon nitride, silicon dioxide or other oxides that interact in some manner with analyte substances. Analyte substances, including interferent substances, interact with the array of microcantilevers 14 to accumulate analyte molecules on the microcantilevers 14, and the controller 18 that cooperates with the array to perform complex algorithms to determine analyte presence, despite background interferent substances. The more molecular properties that can be determined for all of the analytes exposed to the pre-smoke detector 10, the more accurate a decision can be made with regard to marker chemicals that indicate if a potential fire is developing. Such a decision is improved when compared to conventional methods by at least the quantity of properties measured and the orthogonal measurement channels that result, and greatly reduces the percentage of false-positive alarms. And, when a specified analyte and/or threshold level thereof is detected, an alarm associated with the pre-smoke detector 10 can be signaled to warn individuals of a fire or potential fire.

As best shown in FIG. 2, each of the microcantilevers 14 (only one shown here) is provided with a common multi-layer core construction on sensor chip 13, which can be composed of silicon, or other suitable material(s). The microcantilevers 14 may all be attached to sensor chip 13. At the core of the microcantilever 14 is a sandwich structure that includes a metal layer 32/piezoelectric material 26/metal layer 34 that is used for both excitation and sensing. Metal layers 32 and 34 can include, for example, gold, platinum, aluminum, or molybdenum, and the like. Piezoelectric material 26 can include, for example, zinc oxide, lead zirconate titanate, aluminum nitride, or derivatives or combinations thereof. The piezoelectric material 26 may define a unitary piezoelectric drive and sense element 26 for driving and sensing movement of the microcantilever 14. In another embodiment, the sandwiched piezoelectric material 26 can define separate piezoelectric drive and sense elements (not shown). The piezoelectric material 26 may be actuated to drive the microcantilevers 14 when a drive voltage is applied thereto via the drive circuitry 20. For example, the microcantilevers 14 may be driven into oscillation with a periodic voltage, may be deflected with a constant or non-periodic voltage, or may be driven into oscillation with a periodic voltage while being deflected with a constant or non-periodic voltage by drive element. The piezoelectric material 26 can also sense movement of the microcantilevers 14 and cooperates with sense circuitry 22 to relay such information to controller 18. As a further part of the sandwich construction, a resistive heater 38 can be included for heating of the microcantilevers 14, such as for performing specific testing as well as cleaning thereof, and to provide heat sensing functions. The resistive heater 38 may be controlled by controller 18 and can cooperate therewith during application of its heat sensing functions. It should be understood that the microcantilevers 14 can be manufactured, for example, by sputtering processes and other techniques as are known in the art.

In one embodiment, the piezoelectric material 26 of each microcantilever 14 may be connected in series and the lengths of the microcantilevers 14 varied to provide resonant frequency differentiation. The series-connected piezoelectric materials 26 in the array of microcantilevers 14 may be driven with as few as two electrical connections (not shown) thereto. In this instance, scanning the drive voltage through a range of frequency can excite and sense one microcantilever 14 at a time, allowing interrogation of any microcantilever 14 in the array while minimizing the number of electrical connections required. In another configuration, the piezoelectric material 26 of each microcantilever 14 in the array can be connected in parallel, such that as few as two electrical connections (not shown) may be used to drive and sense the microcantilevers 14 and that failure of one microcantilever 14 does not prevent others from operating. In another configuration, the array of microcantilevers 14 is connected in a series-parallel arrangement.

It is expected that the life of a conventional smoke detector or carbon monoxide (CO) detector system is between 5 and 10 years; therefore, in one example, the pre-smoke detector 10 should have a similar lifetime. Yet, while polymer-based sensors and coatings can be very useful in detecting marker chemicals resulting from pyrolysis of smoldering materials, such polymers have a limited lifetime. For example, polymer coatings commonly used for coating quartz crystal microbalances (QCMs) and other sensors generally have a usable life of 1 year. In one embodiment, the surface coating 28 for the microcantilevers 14 of the pre-smoke detector 10 includes a metallic plating or coating, which provides an adhesion-promoting surface that enables the adsorption of analyte molecules and can generally provide an operational lifetime in excess of 10 years.

Of the metals considered for the coating 28 on the microcantilevers 14, examples include molybdenum, palladium, gold, platinum, and/or aluminum, and the like. In the preferred embodiment, those metals with a higher surface energy and, therefore, the highest collection efficiency are selected. While molybdenum is considered to have some corrosion resistance, palladium, gold, and platinum are generally considered to be of the highest corrosion resistance. Thus, in another example, palladium, gold, and platinum are preferred coatings. Aluminum is generally known to be highly prone to corrosion and, therefore, an aluminum coating would be a poor choice for a product with a desired 10-year lifetime requirement. The coating materials may be applied, for example, by standard deposition techniques such as sputter depositions, electron beam depositions, or plasma-enhanced chemical vapor depositions, or by dipping, spraying or dispensing the coating material onto at least a portion of one or more cantilevered probes.

The pre-smoke detector 10, or MPS, in some embodiments supports a variety of thermal, kinetic, and affinity detection processes and methodologies including, but not limited to, those that support detection of the following molecular properties of analyte substances: acidity, basicity, dipolarity, polarizability, dispersion interaction, heat of vaporization, heat of combustion, melting point, resistance capacitance, thermal conductivity, specific heat (heat required to increase temp/unit), activation energy, heat of reaction, heat of hydration, heat of dissociation, boiling point, palladium-hydrogen chemisorption, and/or gold-mercury chemisorption. Thermal detection processes, such as thermogravimetry and differential thermal analysis (DTA), such as when used with metal coated cantilevers, are especially useful for the pre-smoke detector 10 when it must operate in a home or building for extensive periods, e.g., a 10-year lifetime.

The process by which molecules tend to adhere or stick to a surface is called adsorption, which is the adhesion of atoms, ions, biomolecules or molecules of gas, liquid, or dissolved solids to a surface, and is not to be confused with absorption. This adsorption process creates a film of the adsorbate (the molecules or atoms being accumulated) on the surface of the adsorbent. It differs from absorption, in which a fluid permeates or is dissolved by a liquid or solid. The term sorption encompasses both processes, while desorption is the reverse of adsorption. It is a surface phenomenon. Similar to surface tension, adsorption is a consequence of surface energy. In a bulk material, all the bonding requirements (be they ionic, covalent, or metallic) of the constituent atoms of the material are filled by other atoms in the material. However, atoms on the surface of the adsorbent are not wholly surrounded by other adsorbent atoms and, therefore, can attract adsorbates. The exact nature of the bonding depends on the details of the species involved, but the adsorption process is generally classified as physisorption (characteristic of weak van der Waals forces) or chemisorption (characteristic of covalent bonding). It may also occur due to electrostatic attraction. Thus, adsorption will be higher on surfaces with a high surface energy such as metals, compared with low surface energy materials such as polymers, plastics, etc. In addition, adsorption by metal surfaces has the additional advantages of reduced water interference, easier thermal cycling, more thorough thermal cleaning, reduced memory effects, and greater durability versus other candidate surface coatings.

When analyte molecules adhere to the surface coating 28 of the microcantilevers 14, various thermal detection processes can be performed. One of these is thermogravimetry. Thermogravimetry involves the continuous recording of mass changes of a sample of material, as a function of temperature and time. Another detection process that can be performed is differential thermal analysis or DTA. DTA is similar to differential scanning calorimetry. In a DTA detection process, the analyte sample under study and an inert reference (for the pre-smoke detector 10, a cantilever with no analyte present) are made to undergo identical thermal cycles, while recording any temperature difference between the analyte sample and the reference. This differential temperature is then plotted against time or against temperature. Changes in the sample, either exothermic or endothermic, can be detected relative to the inert reference. Thus, a DTA curve provides data on the transformations that have occurred, such as glass transitions, crystallization, melting and sublimation. Since the pre-smoke detector 10 includes multiple cantilevers 14 where analyte samples can adhere and accumulate, the detection processes of DTA and thermogravimetry can optionally be performed in parallel as heat is generated within the microcantilevers 14. And analysis can be performed in cooperation with the piezoelectric material 26, drive and sense circuitry 20 and 22, and the controller 18, for example, to record mass changes. In one example, such tests do not require the presence of polymer coatings and, thus, a 10-year lifetime is possible for the pre-smoke detector.

In addition, it is noted that vapors created by heating (such as during the smoldering and melting stage that precedes the generation of smoke) condense rapidly and more readily on cooler surfaces. It is, therefore, advantageous that the sensor chip 13 in the pre-smoke detector 10 be cooled such that the surface coating 28 of the microcantilevers 14 is cooled to promote analyte adhesion. An effective way to accomplish this is the incorporation of a micro-Peltier device 40 (or other suitable device), as shown in FIG. 3, whose cooling surface 42 is in close proximity to the microcantilevers 14 (not specifically shown in FIG. 3) of the sensor chip 13 of the pre-smoke detector 10.

The Peltier device 40 is a solid-state active pump that can be used here for cooling. In particular, the Peltier device 40 can be placed in the pre-smoke detector 10 such that its cooling surface 42 cools the microcantilevers 14 that are situated within package (or housing) 46, which surrounds the sensor chip 13. An inlet tube 48 permits analyte molecules to enter the package 46 enclosing the sensor chip 13. When incorporated, the Peltier device 40 enhances the ability of the surfaces 28 of the microcantilevers 14 to capture analyte molecules by adsorption. In one example, the Peltier device 40 can reduce the temperature of the microcantilevers 14 by about 40° C. to about 60° C. As a result and with regard to the quantity of analyte molecules of interest that enter the pre-smoke detector 10, a larger percentage of those molecules will be adhered to the surfaces 28 of the microcantilevers 14 than without the Peltier device 40.

Figure 3:
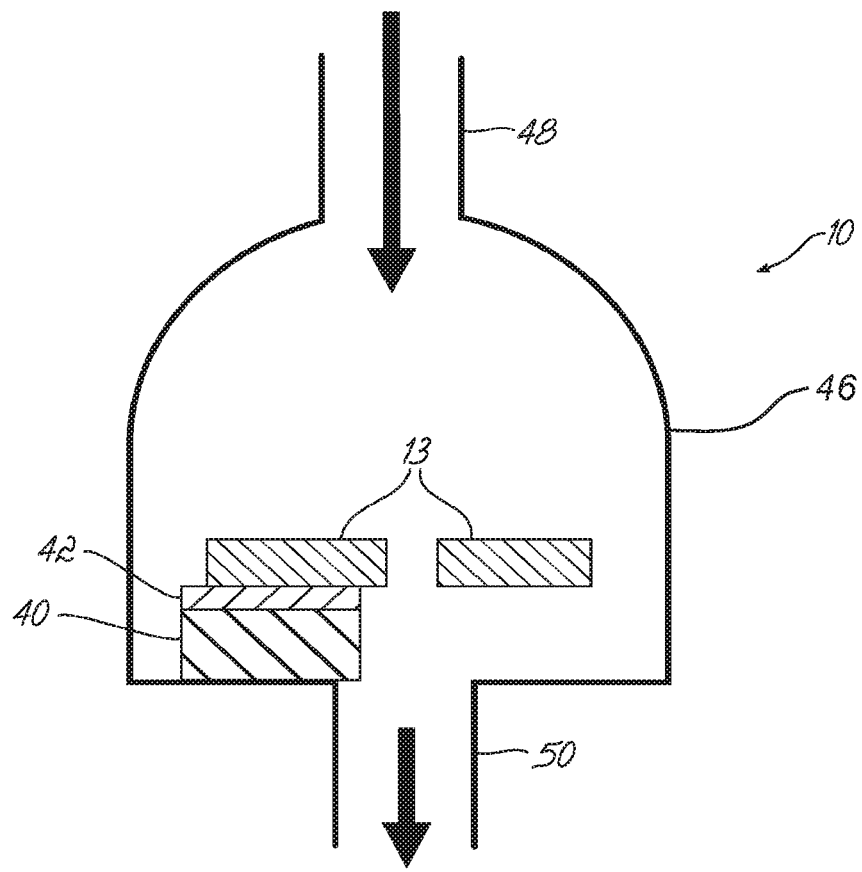
FIG. 3 is a cross-section of the pre-smoke detector as a sensor chip package and including a device for cooling the sensor array chip.

With further reference to FIG. 3, the Peltier device 40 is shown installed within the package 46 of the pre-smoke detector 10 and abutting an internal surface of the package 46 with the cooling surface 42 of the Peltier device 40 being in contact with sensor chip 13 to cool the array of microcantilevers 14 incorporated therein. The sensor chip 13 typically has openings in the center adjacent the microcantilevers 14 to allow analyte vapors to pass near the microcantilevers 14, through the sensor chip 13, and out the outlet 50 of the chip package 46. The Peltier device 40 may be offset as shown in FIG. 3 providing a path for exit vapors to leave through outlet 50.

Figure 4:
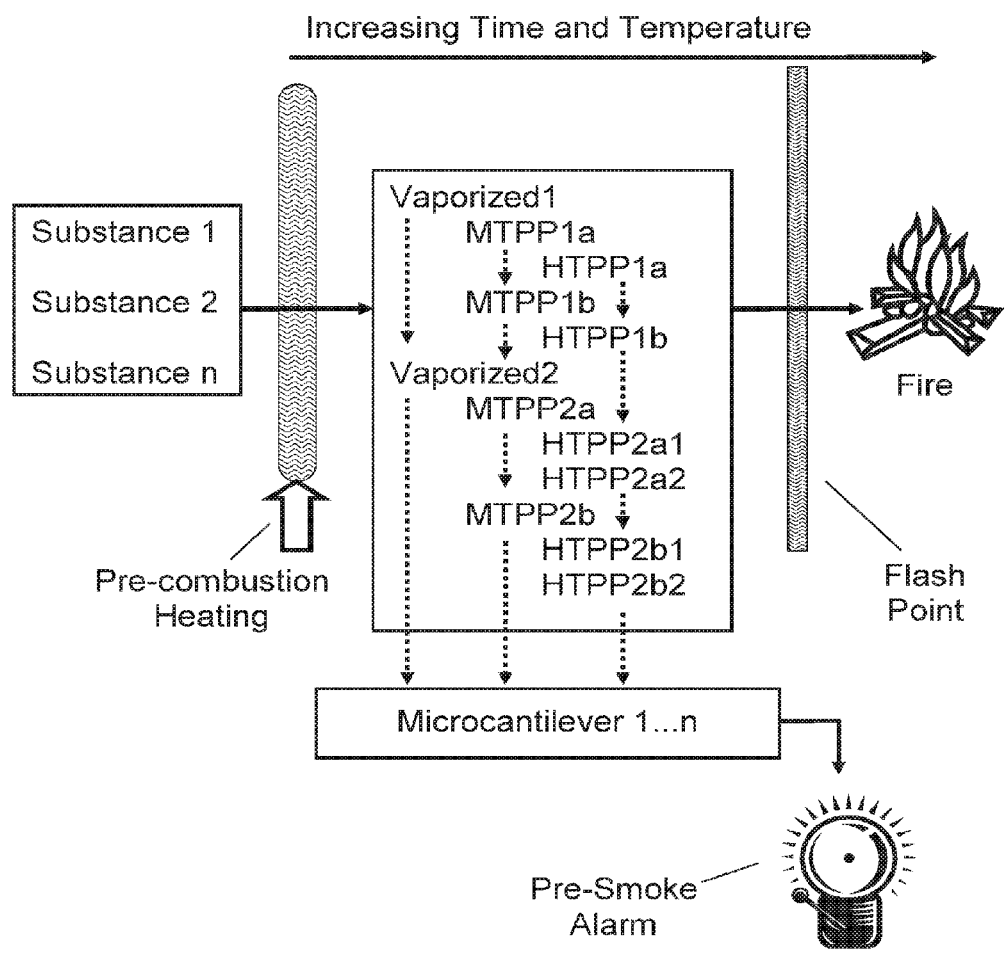
FIG. 4 is a schematic illustration generally depicting how substances and their pyrolysis products are detected at different temperatures and times by the pre-smoke detector as the substances are heated, in accordance with embodiments of the present invention.

With reference now to FIG. 4, a process according to an embodiment of the present invention is shown wherein substances and their pyrolysis products are detected by the microcantilevers 14 of the pre-smoke detector 10 at different temperatures and times as the substances are heated during melting and smoldering in the stage preceding where smoke is generated. Common substances found in homes and buildings that are typically involved in smoldering events due to careless smoking are fabrics used in the manufacture of carpets, upholstery, and clothing. Examples of some of the most common fibers include cotton, rayon, nylon, acrylic, polyester, polylactide (PLA), olefin, and polyurethane. These would be some of the primary substances involved in the pre-smoke stage of a potential fire. The most prevalent primary substances used in wiring insulation materials within a home or building for both appliances and A/C wiring are polyvinyl chloride (PVC), polyethylene, rubber, polychloroprene, and TEFLON®.

During the early stages of melting and/or smoldering, some molecules of a primary substance involved in the pre-smoke stage of a potential fire are vaporized. In FIG. 4, these molecules are indicated as "Vaporized1" and "Vaporized2." As the temperature increases, the primary substances begin to break down or degrade as they undergo the pyrolysis process. The pyrolysis process produces pyrolysis product chemicals which are typically, but not always, smaller molecules than those of the primary substance. The pyrolysis process typically begins between about 200° C. and about 400° C. for many primary substances. This produces medium temperature pyrolysis products, which are indicated in FIG. 4 as MTPP1a and MTPP1b. These are the medium temperature pyrolysis products of primary substances Vaporized1 and Vaporized2. At higher temperatures, the medium temperature pyrolysis products breakdown further and result in yet smaller molecules, indicated in FIG. 4 as high-temperature pyrolysis products HTPP1a, HTPP1b, HTPP2a1, HTPP2a2, HTPP2b1, and HTPP2b2. These high-temperature pyrolysis products are the most volatile and usually precede or coincide with the commencement of smoke, eventually reaching the flashpoint where flame is initiated.

In one example, some or all of the vapors described above are detectable by the microcantilevers 14 of the pre-smoke detector 10, either as individual analytes or as classes of analytes with similar molecular properties. With reference to FIGS. 1, 2, and 4, the operational sequence of the MPS-based pre-smoke detector 10 where the microcantilevers 14 are coated with metallic layers, in one embodiment, is as follows for thermal detection processes. First, analyte molecules are allowed to accumulate on the surface coating 28 of one or more microcantilevers 14 according to the interaction of analyte molecules therewith. During the accumulation time period, the Peltier device 40 (FIG. 3) may be employed if present, to cool the microcantilevers 14. The activation of the Peltier device 40 is performed by centralized timing controller 18. In some embodiments, a pump (not shown) may optionally be included to accelerate the accumulation of analyte molecules.

Once a predetermined time period has passed, centralized timing controller 18 will activate resistive heater 38 in the microcantilevers 14 devoted to thermogravimetric or DTA processes. Subsequently, cantilever temperatures can be stepped in a controlled manner while simultaneously control and excitation drive circuitry 20 provides a drive voltage to induce oscillation in the microcantilevers 14 by exciting the piezoelectric material 26. At the same time, sensing and analysis circuitry 22 allow for the measuring of current through the microcantilevers 14 to determine shifts in resonant frequencies that indicate mass changes as analyte molecules are affected according to the thermogravimetric and DTA processes described earlier, which are analyzed by the controller 18 and its complex algorithms. Heater 38 may also be used for sensing the temperature of the microcantilevers 14 and thus temperature changes may be measured precisely during the heating process. At the end of the time period where heating and analysis are performed, heater 38 in each microcantilever 14 typically heats the microcantilever 14 to a point where any remaining analyte molecules attached to the microcantilever 14 are vaporized, leaving a clean cantilever surface coating 28 to start the next accumulation period.

Before deploying the pre-smoke detector 10, a database is provided associated with the controller 18. That database is the result of training that occurred previously. In particular, during training, analytes of interest are input, and test and analysis cycles are performed to record the results of tests like DTA and thermogravimetry. Common interferents can also be input and the test results also recorded. All of these results are entered into a database that all similar pre-smoke detectors 10 can carry with them. During actual operation, vapor enters the pre-smoke detector 10 and test and analysis cycles can be performed by the controller 18. Specifically, the results can be operated on by software that performs pattern matching and analysis to determine what analytes are present while sorting out and excluding the interferents. When a positive identification is made on key marker analytes that indicate the presence of smoldering material, for example, the alarm of the pre-smoke detector 10 can be activated. The system may also alternatively or additionally determine, for example, that the mass of such marker analytes is present in an amount that passes a previously determined threshold level, and as a result of reaching that level, the alarm is activated.

With continuing reference to FIG. 4, after a flashpoint is reached, chemical vapors continue to be given off in addition to smoke particles as the primary flammable substances and their pyrolysis product vapors continue to breakdown. At this point in the evolutionary process of a fire, the pre-smoke detector 10 will also detect these chemical vapors and in doing so provide additional detection redundancy if a conventional particle-type smoke detection is also utilized at the same location. Detection of the analyte(s) should be performed with a degree of selectivity such that background interferent substances do not negatively influence the desired detection result. Some common interferents in the home include, but are not limited to, tobacco smoke; new carpet; new furniture; new electronic equipment; vapors produced by cooking—in particular vapors produced by the breakdown of fat, grease, and oil; personal care products; cleaning products; perfumes and fragrances; air fresheners; pet-related odors; and byproducts of the burning of propane and natural gas, and related taggants and contaminants when these gasses are burnt for heating and cooking purposes.

In theory, it is understood that the vaporized molecules of the primary substance(s) are most desirable to detect since these vapors are emitted early in the melting/smoldering process. However, when new products are brought into a home such as new furniture or new carpet, or when a home is newly constructed, concentration levels in air for molecules of the primary substance typically increase significantly, as often noticed by the human nose. This increased concentration is not indicative of a danger, and the pre-smoke detector should not alarm under this condition or due to the presence of any common household interferent. Therefore, in one example, the most reliable early warning detection will be that of the medium temperature pyrolysis products of the primary substances, typically produced between 200° C. and 400° C. And when a threshold level of medium temperature pyrolysis products are detected by the pre-smoke detector 10, an alarm is sounded warning individuals of a fire or the potential for a fire.

Concerning residential smoke detectors, these are by their nature, low cost items. The pre-smoke detector 10 should, therefore, be relatively low cost to be successfully deployed. In one example, the microchip-based sensor chip 13 is the best choice. The pre-smoke detector 10 should detect a breadth of chemicals and the pyrolysis products derived from those chemicals commonly used in fabrics and wiring insulation used in the home. Thus, a high level of selectivity is required for detecting a large number of analytes in the presence of common household interferents.

Another consideration for the pre-smoke detector 10 is the propensity of analyte molecules to rise or not rise when released from smoldering material. Conventional smoke detectors are typically located near the ceiling of a room. The overwhelming majority of both medium and high-temperature pyrolysis products for household fabrics and wiring insulation are heavier than air in the vapor phase. Thus, if a room is to have a single pre-smoke detector 10, in one example, it may be located approximate or adjacent the floor. A pre-smoke detector 10 that plugs directly into an AC outlet near the floor could accomplish this goal. In one embodiment, a preferred solution would be a dedicated pre-smoke detector that is located near the floor, wired into the smoke detector alarm network, and adheres to the detector network alarm protocol when a building has a detector network installed. Carbon monoxide (CO) detectors have recently become popular and are now being combined with conventional smoke detectors in the same units, typically mounted near the ceiling of a room. CO has a density of 0.97 compared with air and is, therefore, slightly lighter. CO diffuses readily with air and is usually present at most heights in a room, however for efficiency of space and cost, as well as convenience of installation, the motivation to combine CO detectors with conventional smoke detectors is making the combined solution a common scenario. For chemicals given off during the pre-ignition stage of a fire, such a solution is not acceptable.

Figure 5A:
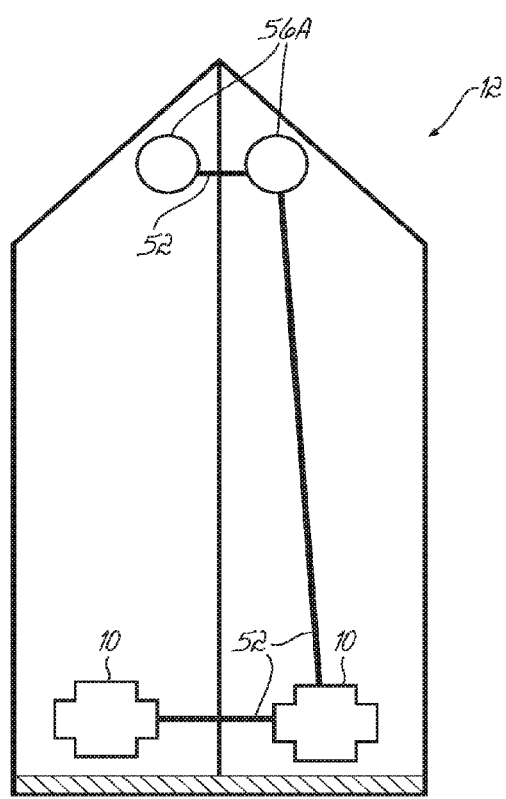
FIG. 5A is a cross-sectional view of one embodiment of a pre-smoke detector system hardwired in a home with conventional smoke detectors.
Figure 5B:
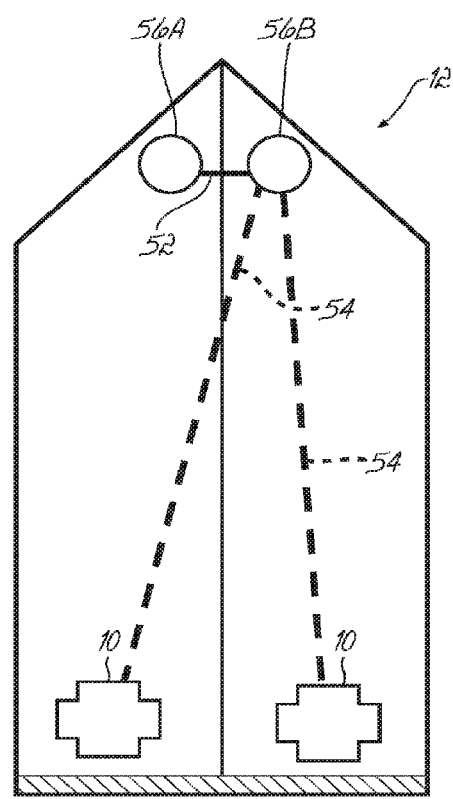
FIG. 5B is a cross-sectional view similar to FIG. 5A but showing another embodiment of a pre-smoke detector system in a home with conventional smoke detectors and having wireless communication capabilities.

With further reference now to FIGS. 5A and 5B, a pre-smoke detector system 12 is shown wherein pre-smoke detectors 10 are mounted near floor level to sense heavier-than-air gases or vapors, which can be early indicators of an impending fire. It should be understood that any number of pre-smoke detectors 10 (1, 2, or more) may be employed in a single room or structure. The pre-smoke detectors 10 can be connected to hardwired or wireless smoke detectors 56A and 56B, which detect smoke particles, by a dedicated smoke-detector wiring system, wirelessly, or a combination thereof and their alarm network, which exist in most homes today, usually by building code mandate. Some smoke detector manufacturers offer units that connect to the wired alarm network, but also offer a wireless capability that can communicate with "wireless" detectors, enabling additional pre-smoke detectors to be added where wiring is not a convenient option.

With specific reference to FIG. 5A, pre-smoke detectors 10 are installed near the floor in two rooms of a home in addition to hardwired smoke detectors 56A, which are installed near the ceiling. All are connected together by a wired alarm network 52 of the type commonly known in the art. In FIG. 5B, pre-smoke detectors 10 with wireless communication capability are installed near the floor and communicate wirelessly 54 with wireless smoke detector 56B that is wireless enabled, which in turn is connected to a wired alarm network 52 and hardwired smoke detector 56A. When adding pre-smoke detector(s) 10, which has wireless capabilities, into a home, for example, with all hardwired smoke detectors 56A that are wired together, one need only replace one of the hardwired smoke detectors 56A with a wireless-enabled smoke detector 56B. In FIGS. 5A and 5B, pre-smoke detectors 10 may be designed such that they plug into a power outlet near the floor, rather than being mounted to a junction box. In addition to the foregoing alternative alarm communication mechanisms, pre-smoke detectors 10 may be wireless-enabled 54 with all wireless smoke detectors 56B and communicate with each other wirelessly.

The foregoing description of preferred embodiments of the present invention has been provided for the purposes of illustration and description. It is not intended to be exhaustive or to limit the invention to the precise forms disclosed. Many modifications and variations will be apparent to one of ordinary skill in the relevant arts. For example, steps preformed in the embodiments of the invention disclosed can be performed in alternate orders, certain steps can be omitted, and additional steps can be added. Structural variations of combinations of features amongst embodiments will also become apparent to those skilled in the art. The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the claims and their equivalents.

What is claimed is:

1. A method of determining an early stage of a fire, the method comprising:
    exposing a sensor comprising an array of microcantilevers to a vapor comprising at least one vaporized pyrolysis product, the array of microcantilevers comprising at least one microcantilever having a chemical sensitive coating different than a chemical sensitive coating of at least one other microcantilever;
    adsorbing the at least one vaporized pyrolysis product on a chemical sensitive coating of the at least one microcantilever of the array of microcantilevers;
    detecting a presence of the at least one vaporized pyrolysis product on the chemical sensitive coating of the at least one microcantilever; and
    heating the at least one microcantilever to a temperature sufficient to vaporize adsorbed pyrolysis products from the chemical sensitive coating to clean the at least one microcantilever.

2. The method of claim 1, wherein detecting a presence of the at least one vaporized pyrolysis product comprises measuring mass changes on the at least one microcantilever as a function of temperature and time.

3. The method of claim 1, wherein detecting a presence of the at least one vaporized pyrolysis product comprises:
    exposing at least one reference microcantilever and the at least one microcantilever to at least one thermal cycle; and
    determining a difference in temperature between the at least one reference microcantilever and the at least one microcantilever.

4. The method of claim 3, further comprising monitoring the difference in temperature as a function of time or temperature.

5. The method of claim 1, wherein detecting a presence of the at least one vaporized pyrolysis product comprises performing differential thermal analysis and thermogravimetry simultaneously using the array of microcantilevers.

6. The method of claim 1, further comprising increasing a temperature of the microcantilevers of the array of microcantilevers in a stepped manner while exposing a piezoelectric material associated with each microcantilever to a drive voltage to oscillate the microcantilevers of the array of microcantilevers.

7. The method of claim 6, further comprising determining a shift in resonant frequency of the at least one microcantilever while oscillating the microcantilevers of the array of microcantilevers.

8. The method of claim 6, further comprising determining a temperature of the microcantilevers of the array of microcantilevers with a resistive heater associated with each microcantilever.

9. The method of claim 1, further comprising adsorbing at least one vaporized pyrolysis product on the chemical sensitive coating of the at least one microcantilever after cleaning the at least one microcantilever.

10. A method of determining a presence of pyrolysis products with a pre-smoke detector, the method comprising:
    exposing an array of microcantilevers to a vapor comprising pyrolysis products;
    adsorbing at least one pyrolysis product on a chemical sensitive coating of at least one microcantilever of the array of microcantilevers;
    driving a piezoelectric material associated with each microcantilever of the array of microcantilevers to oscillate each microcantilever of the array of microcantilevers;
    driving, with a controller, a resistive heater of the at least one microcantilever and ramping a temperature thereof while simultaneously oscillating the at least one microcantilever;
    measuring a shift in resonant frequency of the at least one microcantilever while oscillating the at least one microcantilever; and
    heating the at least one microcantilever after measuring the shift in the resonant frequency to vaporize adsorbed pyrolysis products on the at least one microcantilever and clean a surface thereof.

11. The method of claim 10, further comprising activating an alarm responsive to detecting more than a predetermined amount of the pyrolysis products.

12. The method of claim 10, wherein exposing an array of microcantilevers to a vapor comprising pyrolysis products comprises exposing the sensor to a vapor comprising pyrolysis products of at least one of cotton, rayon, nylon, acrylic, polyester, polyactide, olefin, polyurethane, polyvinyl chloride, polyethylene, rubber, and polychloroprene formed at temperatures between 200° C. and 400° C.

13. A system for early detection of a fire, the system comprising:
    a pre-smoke detector, comprising:
        an array of microcantilevers on a sensor chip, at least one microcantilever of the array of microcantilevers comprising a chemical sensitive coating formulated to adsorb at least one pyrolysis product different from a chemical sensitive coating of at least another microcantilever of the array of microcantilevers;
        a resistive heater associated with the at least one microcantilever, the resistive heater configured to heat and sense a temperature of the at least one microcantilever;
        an electronic circuit comprising drive and sense circuitry to respectively drive and sense deflection of the microcantilevers of the array of microcantilevers; and
    a controller, the controller configured to:
        detect pyrolysis products adsorbed on the at least one microcantilever; and
        heat the at least one microcantilever after detecting the pyrolysis products adsorbed on the at least one microcantilever to remove the adsorbed pyrolysis products and clean a surface of the at least one microcantilever.

14. The system of claim 13, wherein the array of microcantilevers is disposed on a single substrate.

15. The system of claim 13, wherein at least one microcantilever of the array of microcantilevers comprises an inert coating material.

16. The system of claim 13, wherein the chemical sensitive coating of the at least one microcantilever and the chemical sensitive coating of the at least another microcantilever do not comprise a polymer.

17. The system of claim 13, wherein the at least one microcantilever has a different length than at least another microcantilever of the array of microcantilevers.

18. The system of claim 13, wherein the chemical sensitive coating of the at least one microcantilever comprises a metal.

19. The system of claim 13, wherein the at least one microcantilever exhibits a different resonant frequency than a resonant frequency of the at least another microcantilever.

20. The system of claim 13, wherein the controller is further configured to increase a temperature of the microcantilevers of the array of microcantilevers in a stepped manner while exposing a piezoelectric material associated with each microcantilever to a drive voltage.

21. The system of claim 13, wherein each microcantilever of the array of microcantilevers comprises a piezoelectric material, the piezoelectric material of each microcantilever electrically connected to the piezoelectric material of the other microcantilevers in series.

22. The system of claim 13, further comprising a smoke detector connected to the pre-smoke detector with at least one of a wired connection or a wireless connection.

* * * * *